United States Patent [19]

Zacharias

[11] Patent Number: 4,523,455

[45] Date of Patent: Jun. 18, 1985

[54] TUBE TESTING PRESSES

[75] Inventor: Theodor Zacharias, Meerbusch, Fed. Rep. of Germany

[73] Assignee: Kocks Technik GmbH & Co., Hilden, Fed. Rep. of Germany

[21] Appl. No.: 530,963

[22] Filed: Sep. 12, 1983

[30] Foreign Application Priority Data

Nov. 23, 1982 [DE] Fed. Rep. of Germany ....... 3243201

[51] Int. Cl.$^3$ ............................................. G01M 3/28
[52] U.S. Cl. ..................... 73/49.5; 73/49.8; 138/90
[58] Field of Search ...................... 73/49.5, 49.8, 49.1; 138/90

[56] References Cited

U.S. PATENT DOCUMENTS

| | | | |
|---|---|---|---|
| 2,655,182 | 10/1953 | Hayes et al. | 138/90 |
| 2,873,764 | 2/1959 | Lombard et al. | 73/49.5 X |
| 3,331,238 | 7/1967 | Kost et al. | 73/49.5 |
| 3,803,901 | 4/1974 | McConnell et al. | 138/90 X |
| 4,127,026 | 11/1978 | Battafarano | 73/49.5 |

Primary Examiner—Stewart J. Levy
Assistant Examiner—Joseph W. Roskos
Attorney, Agent, or Firm—Buell, Ziesenheim, Beck & Alstadt

[57] ABSTRACT

The invention concerns a press for the testing by means of internal pressure of tubes provided with threaded ends, in which end pieces screwed in a pressure medium-tight manner on the tube ends are inserted into the sealing heads of the press. The end pieces are cap-like and have radially arranged connecting boreholes so that the pressure medium feed is radial in contrast to the axial pressure medium feed of the familiar constructions. No appreciable axial forces thus arise between the tubes and the test heads. In addition, the outer end of the cap-like end pieces facing away from the tube serves for the coupling of a shaft, which can displace the tube with the end piece axially and act upon it with a torque. Furthermore, the sealing head is readily detachable in a like manner in a retaining head and is inserted pressure medium-tight to the outside, just as the end pieces in the sealing heads.

5 Claims, 1 Drawing Figure

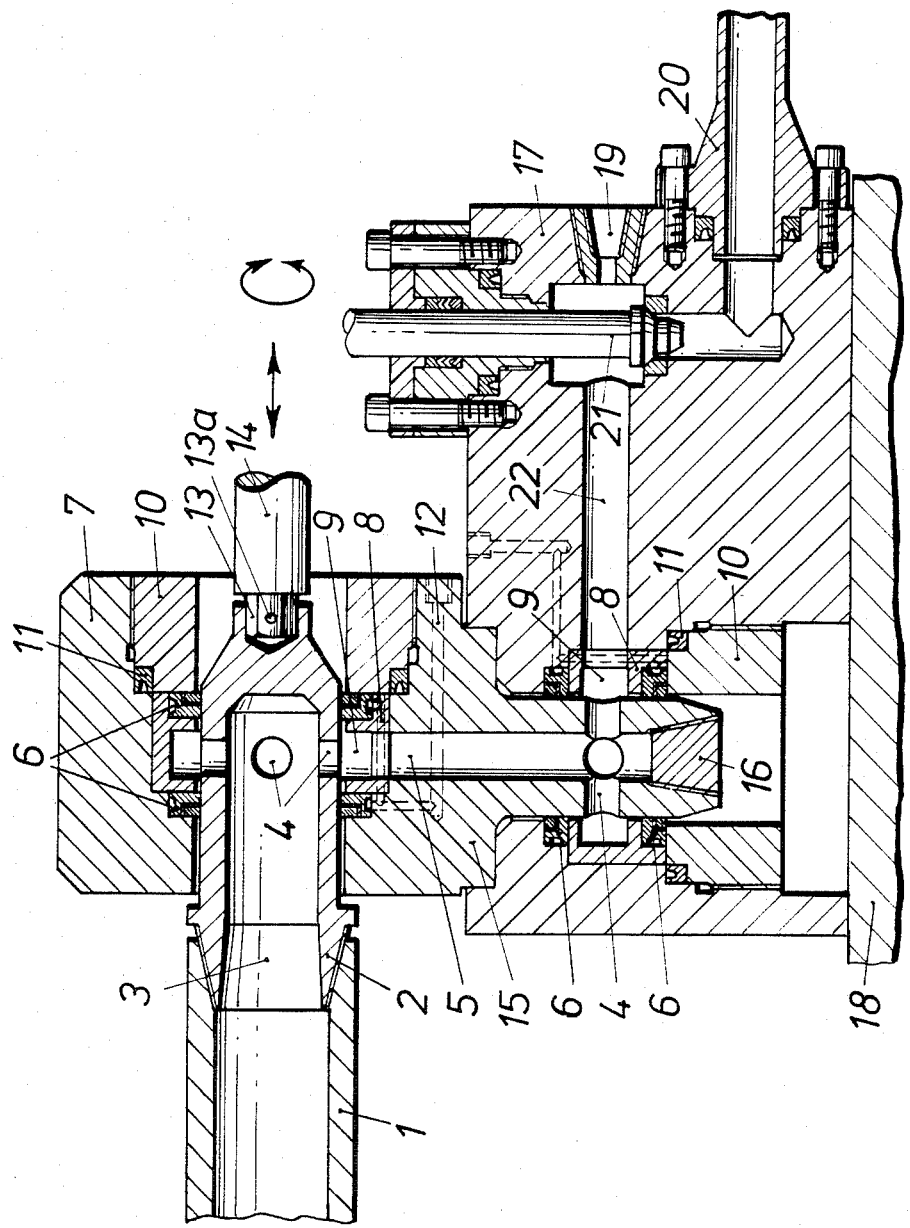

TUBE TESTING PRESSES

This invention relates to tube testing presses and more particularly to a press for testing tubes with threaded ends by means of an internal pressure, in which end pieces screwed in a pressure medium-tight manner on the tube ends are inserted into the sealing heads of the press, these end pieces have outer surfaces on which seals inserted into the sealing heads lie in a pressure medium-tight manner and in which the end pieces have axial boreholes that connect the inner space of the tube with the pressure medium feed and drain lines of the press.

In a familiar press of this type (DE-AS No. 10 31 996) the screwed-on end pieces are sleeve-shaped, i.e., the axial boreholes pass through the end pieces over their entire length. Surfaces are thus formed, on which the high pressure of the pressure medium acts during testing so that substantial axial forces load the tube to be tested and also the press during the testing process. The result is that the tubes must withstand high axial forces simultaneously with the actual testing pressure, which readily results in buckling during the testing process, especially in tubes with relatively small diameters and with a high axial compression stress. The press must also be sturdy so that it is capable of absorbing the axial forces that arise. In addition, the middle of the sealing heads on the side facing away from the tubes in the familiar construction serves to feed and drain away the pressure medium and/or the air contained in the tubes, so that nothing else can be arranged at this site of the sealing heads. It is also necessary to connect the sealing heads with the support of the press in a particularly stable and secure manner so that the axial forces acting first on the sealing heads can also be harmlessly transfered to the supporting frame of the press. This in turn necessitates a substantial labor cost for the attending personnel if the sealing heads of the press have to be exchanged, e.g., in the case of a dimension change with a greater size difference of the tubes to be tested, and relatively long stoppage times result.

The present invention proposes a press of the above nentioned type, which can be manipulated more simply, is kinder to the tube to be tested, and offers the possibility of better testing.

This problem is resolved according to the present invention by designing the end pieces with axial boreholes closed on the end in the form of a cap and such that there is at least one essentially radial connecting borehole to the axial borehole, which empties between two seals arranged with an axial spacing in the sealing heads in the region of a pressure medium feed or drain line.

Due to the cap-like design of the end pieces and the essentially radial feed of the pressure medium through the cone connecting boreholes, the axial tractive or compressive force between the tubes to be tested and the sealing heads is avoided. Furthermore, there are no axial forces between the sealing heads gripping the tube. The sealing heads must be fastened so solidly to the supporting frame of the press as required by their own weight and the weight of the tube to be tested without having to take into account the very high testing pressure and the high axial forces that arise in the familiar construction. Due to the falling away of these high axial forces that arise as a result of the testing pressure, the supporting frame of the test press can be constructed considerably lighter and less expensively. The means of fastening the sealing heads on the press support frame can be effected without difficulty so that a rapid and troublefree replacement of the sealing heads is possible. For example, in the case of a dimension change of the tube to be tested, the press is again quickly ready for use. The central zone of the sealing heads on the side facing away from the tubes is also completely free because the pressure medium feed and drain as well as the deaeration take place in the radial direction. This construction of the sealing heads also facilitates quite substantially the replacement of the seals because they are accessible from two opposite sides.

In a preferred embodiment of the invention, the end pieces are provided on their outer end surface facing away from the tube with a coupling element, preferably an internal or external hexagon, for the insertion of a driveable shaft for the rotation and/or axial displacement of the end piece. This implementation form permits the tube to be tested to be acted upon by a torque, which can be applied both during and also before and after the testing by means of internal pressure. If one considers that many tubes are subjected to substantial torsion in practice, e.g., pipes for drill stems, such a testing can then be of considerable advantage. In addition, the tube to be tested or already tested can in this manner, with the aid of the shaft, be drawn into the sealing head or extracted from it. Furthermore, the cap-like end pieces can be screwed on or in the tube ends with the aid of the shaft in a pressure medium-tight manner, in which case the tube is held by the feed arrangements otherwise required.

In another embodiment of the invention the sealing heads can also have a cap-like end piece, with which they are slipped into a retaining head corresponding to the sealing head in a pressure medium-tight outward and rapidly exchangeable manner. The above inventive principle of the axial force-free reception of the tube to be tested in the sealing heads is thus also utilized in the sealing heads themselves, in that the latter are in turn inserted free of axial forces into the retaining heads, which are fastened solidly with the support frame of the press or are a component part of it. This has the advantage that the sealing heads, just as the tubes, can be rapidly exchanged if this should be necessary in the case of a dimensional change in the tubes with particularly large size differences or in replacing the seals. Because the sealing heads, especially in the case of large tube dimensions, have substantial sizes and weights and because the high pressure of the pressure medium must also be conveyed through the coupling point between the sealing heads and their mounting at the support frame of the press, very sturdy and difficultly detachable fastening means must be used in the familiar constructions. The use of cap-like end pieces according to the invention at these sites also results in a substantial simplification of the construction and a substantial reduction in the labor expended in assembling and disassembling the sealing heads. The above is all the more valid if the difficulties at the sealing sites and the mechanical expenditure increase with the continuous requirements for higher testing pressures.

In the foregoing general description certain objects, purposes and advantages of this invention have been set out. Other objects, purposes and advantages of the invention will be apparent from the following description and the accompanying drawing.

The drawing shows a section through a press according to the present invention.

The invention is illustrated in the accompanying drawing by means of an implemented example. A tube to be tested, of which only an end section can be seen and which has an internal thread, is designated by 1. A cap-like end piece 2 provided with an external thread is screwed pressure medium-tight on the end of the tube 1. Of course, it is also possible for the tube 1 to have an external thread and the end piece 2 to have a corresponding internal thread. The end piece 2 has an axial borehole 3, which is closed cap-like on the side facing away from the tube 1. Several radial connecting boreholes 4 arranged on the periphery connect the axial borehole 3 with a pressure medium feed or drain line 5, which can also be used for introducing or removing air. The connecting boreholes 4 empty between two seals 6 arranged with an axial spacing; these seals can be designed, for example, in accordance with FIG. 2 of DE-PS No. 12 30 246. The seals 6 are inserted into a sealing head 7 and are held by a spacer ring 8 to a spacing that simultaneously forms an annular space 9 for connecting all the connecting boreholes 4 together. A threaded ring 10 holds the seals 6 and the spacer ring 8 in the sealing head 7, in which case an additional sealing ring 11 prevents any outflow of the pressure medium. For the seals 6 to be effective, they should be acted upon by a certain minimum pressure. This supply pressure is conveyed through a line 21 before the actual pressure medium for testing the tube 1 flows in.

The end piece 2 is provided on its outer face facing away from the tube 1 with an internal hexagon 13 and a pin 13a, which serve as the coupling element, via which a driveable shaft 14 is coupled with the end piece 2, such that an axial and a rotational movement of the shaft 14 can be transfered to the end piece 2.

The sealing head 7 also has a cap-like end piece 15, also in one piece with it, which is designed in principle identically as the end piece 2, except that it is not screwed onto a tube end, but is a part of the sealing head 7. The end piece 15 is provided on its end facing away from the tube 1 with a plug 16 that closes an axial borehole that serves as the pressure medium feed and drain line 5 and which corresponds to the axial borehole 3 in the end piece 2. The end piece 15 is inserted into a retaining head 17 that is fastened solidly on the support frame 18 of the press. The sealing of the end piece 15 inside of the retaining head 17 is designed in the same manner as the sealing between the end piece 2 and sealing head 7, such that the same reference numbers were used for the comparable parts.

Two different connections 19 and 20 are provided on the retaining head 17. For filling or emptying the tube 1, the connection 20 with its larger cross section is used. If the tube 1 is filled, the valve designated by 21 is closed and the test pressure is fed through the second connection 19, which is connected with a high-pressure line (not shown), through a line 22 to the line 5 and through the latter to the inner space of the tube 1.

In the foregoing specification I have set out certain preferred practices and embodiments of this invention, however, it will be understood that this invention may be otherwise embodied within the scope of the following claims.

I claim:

1. Press for testing tubes provided with threaded ends by means of internal pressure comprising end pieces having threads at one end adapted to be screwed pressure medium-tight on the tube ends, a press body, sealing heads on the press body, said end pieces having outer surfaces at the end opposite the threaded end on which axially spaced seals inserted in the sealing head lie in a pressure medium-tight manner, the end pieces having cap-like axial boreholes closed on the end opposite the threaded end and having at least one essentially radial connecting borehole in said end opposite the threaded end connected to the axial borehole, said radial bore hole empties between two seals arranged with an axial spacing in the sealing heads in the zone of a pressure medium feed or drain line.

2. Press according to claim 1, characterized in that the end pieces are provided on their outer end surface facing away from the tube with a coupling element for engaging on a driveable shaft for the rotation and/or axial displacement of the end piece.

3. Press according to claims 1 or 2, characterized in that the sealing heads have a cap-like end piece with which they are inserted into a retaining head corresponding to the sealing head and are pressure medium-tight to the outside and rapidly exchangeable.

4. Press according to claim 2 wherein the coupling element is an internal hexagon.

5. Press according to claim 2 wherein the coupling element is an external hexagon.

* * * * *